(12) United States Patent
Gui et al.

(10) Patent No.: US 9,199,068 B2
(45) Date of Patent: Dec. 1, 2015

(54) BALLOON DILATATION CATHETER PROVIDED WITH SOFT COATING

(75) Inventors: Hannah Gui, Dongguan (CN); Will Chen, Dongguan (CN)

(73) Assignee: Dongguan Dikai Medical Co., Ltd., Dongguan, Guangdong Province (CN)

( * ) Notice: Subject to any disclaimer, the term of this patent is extended or adjusted under 35 U.S.C. 154(b) by 216 days.

(21) Appl. No.: 13/809,160

(22) PCT Filed: Dec. 14, 2011

(86) PCT No.: PCT/CN2011/083961
§ 371 (c)(1),
(2), (4) Date: Jan. 8, 2013

(87) PCT Pub. No.: WO2013/086700
PCT Pub. Date: Jun. 20, 2013

(65) Prior Publication Data
US 2013/0158590 A1   Jun. 20, 2013

(51) Int. Cl.
A61M 29/00    (2006.01)
A61M 29/02    (2006.01)
A61M 25/10    (2013.01)
A61M 25/00    (2006.01)

(52) U.S. Cl.
CPC ............. *A61M 29/02* (2013.01); *A61M 25/104* (2013.01); *A61M 25/0045* (2013.01); *A61M 2025/0081* (2013.01); *A61M 2025/1088* (2013.01); *A61M 2025/1093* (2013.01)

(58) Field of Classification Search
CPC   A61M 29/02; A61M 25/104; A61M 25/0045
USPC .................................. 606/191, 192; 604/509
See application file for complete search history.

(56) References Cited

U.S. PATENT DOCUMENTS 6,623,504 B2 *   9/2003   Vrba et al. .................... 606/192

* cited by examiner

*Primary Examiner* — Victor Nguyen
(74) *Attorney, Agent, or Firm* — Novoclaims Patent Sevices LLC; Mei Lin Wong

(57) ABSTRACT

The present invention relates to technical field of cardiac medical instruments, and more particularly to a balloon dilatation catheter provided with soft coating tip. In the balloon dilatation catheter provided with soft coating tip of the present invention, the balloon dilatation catheter comprises a balloon, and inner catheter. A distal end of the balloon at a terminal end of the inner catheter extends outward to form a catheter tip with taper inner cavity. A tip coating layer made of a material which is softer than a material of the balloon is coated on the catheter tip. The material of the balloon generally selects a relatively hard material. The distal end of the balloon extends outward to form a catheter tip. The material forming the inner cavity is harder, so that the inner layer the tip with greater hardness together with the inner hydrophilic coating layer can effectively reduce the occurrence of the dead lock toward the guide wire, so as to ensure the unhindered operation of a surgery and anti reduce the occurrence of medic it accidents. When in a operation with a tip coating layer made of a material which is softer than a material of the balloon is coated on the catheter tip, the injury to the blood vessel when the tip is having contact with the blood vessel is minimized so that a further injury to the cardiovascular system of the patient is prevented.

2 Claims, 1 Drawing Sheet

BALLOON DILATATION CATHETER PROVIDED WITH SOFT COATING

BACKGROUND OF THE PRESENT INVENTION

1. Field of Invention

The present invention relates to technical field of cardiac medical instruments, and more particularly to a balloon dilatation catheter provided with soft coating tip.

2. Description of Related Arts

In the medical field, the percutaneous transluminal coronary angioplasty has become mature gradually. As the key mechanical devices of this technology, the balloon dilatation catheters have been upgraded fast with the development of the technology. The PTCA process typically comprises advancing the guiding catheter via skin penetrating within the femoral artery or skin artery so as to address the distal end of the guiding catheter at the entrance of coronary artery, after locating the guiding artery, guiding a balloon dilatation catheter to pass through the guiding artery into the coronary artery, wherein the balloon dilatation catheter generally is used with a small-diameter operative guide wire which can be operated to enter into the selected artery branch to be cured, and then transferring the balloon dilatation catheter which is in a shrinking state together with the anastomotic guide wire to a constricted area, and finally inflating the balloon 1 to expand the constricted artery for purpose of cure.

Currently, a conventional catheter tip 3 of the PTCA balloon dilatation catheter in the market generally employs a structure in which an inner catheter 2 is directly weld to the catheter tip 3, wherein a prolonged section it of the balloon 1 is used for coating the connection thereof prior to the welding process. The current tips are divided into two groups in concern of the selected material: one is soft tip, and the other is relatively hard tip. The soft tip is advantageous for its good softness and being resulting in less injury to a blood vessel. Since its good adhering ability with the guide wire, the flexibility of the dilation catheter is effectively enhanced and thus currently the soft tip serves as the main tip material. The shortcomings of the soft tip in use are also obvious. The inner catheter and the tip both uses soft materials, even if the interior of the catheter and the guide wire are all coated with lubricating layers, but the soft material of resilient feature has a strong coating ability and may easy to result in a dead lock when the catheter is exerted with a relatively large force at a corner, thus the guide wire cannot rotate freely and most often the surgery simply cannot go on. When the relatively hard tip is used, the most vital to disadvantage is that it may result in a wound to the blood vessel tissue and cause a further injury to the cardiovascular system of the patient.

SUMMARY OF THE PRESENT INVENTION

In view of the problem that there is dead lock of the guide wire at the tip of the current PTCA balloon dilatation catheter as well as the problem that it may cause a further injury to the patient, the present invention provides a balloon dilatation catheter with soft coating tip for addressing these above problems.

Additional advantages and features of the invention will become apparent from the description which follows, and may be realized by means of the instrumentalities and combinations particular point out in the appended claims.

According to the present invention, the foregoing and other objects and advantages are attained by a balloon dilatation catheter provided with soft coating tip, wherein the balloon dilatation catheter comprises a balloon, and an inner catheter, wherein a distal end of the balloon at as terminal end of the inner catheter extends outward to form a catheter tip with taper inner cavity, wherein a up coating layer made of a material which is softer than a material of the balloon is coated on the catheter tip.

A coating of the tip coating layer extends to an end surface of the catheter tip wherein the coating layer comprises a round corner setting provided at an outer circumference at a distal end thereof.

A catheter wall of the terminal end of the inner catheter has a gradually decreasing thickness toward a tip end thereof and is bonded with an outer extending section at the distal end of the balloon without obvious stepped locations of bonding.

A catheter wall of the catheter tip formed from an outer extending section of the distal end of the balloon has a gradually decreasing thickness, wherein an outward extending wall of the coating layer has a gradually increasing thickness, wherein a catheter wall formed by the extending section of the distal end of the balloon and the coating layer has an evenly distributed thickness, wherein bond locations are unhindered and smooth.

An outer extending section of the distal end of the balloon has a hardness ranged from Shore hardness 55 to 90, wherein the coating layer has a hardness ranged from Shore hardness 30 to 55.

The present invention is advantageous in that in the balloon dilatation catheter provided with soft coating tip of the present invention, the balloon dilatation catheter comprises a balloon, and an inner catheter. A distal end of the balloon at a terminal end of the inner catheter extends outward to form a catheter tip with taper inner cavity. A tip coating layer made of a material which is softer than a material of the balloon is coated on the catheter tip. The material of the balloon generally selects a relatively hard material. The distal end of the balloon extends outward to form a catheter tip. The material forming the inner cavity is harder, so that the inner layer of the tip with greater hardness together with the inner hydrophilic coating layer can effectively reduce the occurrence of the dead lock toward the guide wire, so as to ensure the unhindered operation of a surgery and reduce the occurrence of medical accidents. When in a operation with a tip coating layer made of a material which is softer than a material of the balloon is coated on the catheter tip, the injury to the blood vessel when the tip is having contact with the blood vessel is minimized so that a further injury to the cardiovascular system of the patient is prevented.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferable embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
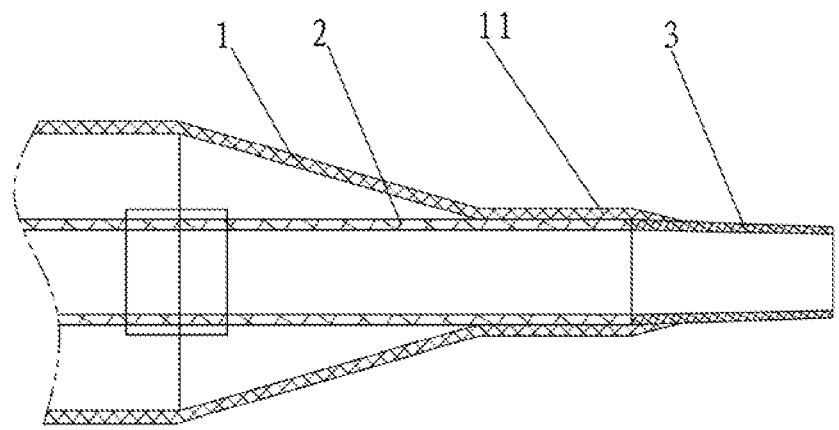
FIG. 1 is a schematic view of a balloon dilatation catheter according to the prior art.
Figure 2:
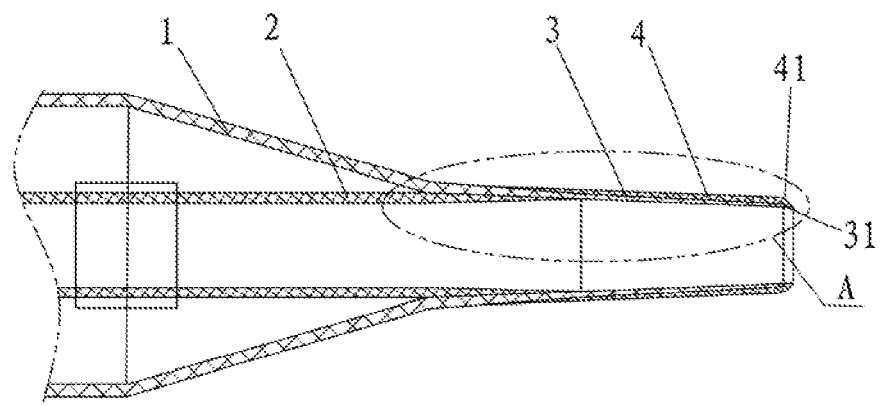
FIG. 2 is a schematic view of the present invention.
Figure 3:
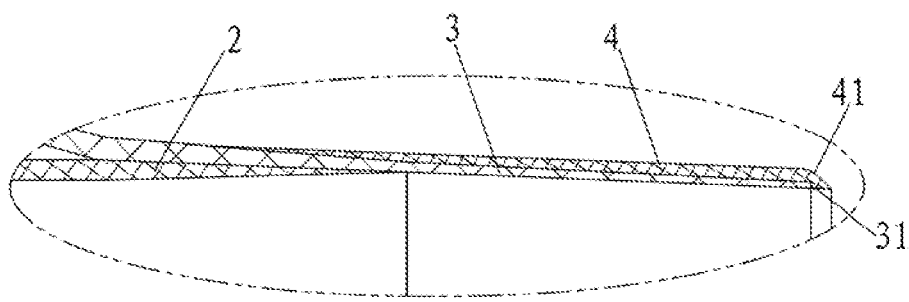
FIG. 3 is an enlarged partial view of A in FIG. 2.

Referring to FIG. 2 and FIG. 3, the balloon dilatation catheter provided with soft coating tip of the present invention is illustrated in details in the following description. The balloon dilatation catheter comprises a balloon 1, and an inner catheter 2. A distal end of the balloon 1 at a terminal end of the inner catheter 2 extends outward to form a catheter tip 3 with taper inner cavity. A tip coating layer 4 made of a material which is softer dun a material of the balloon 1 is coated on the catheter tip 3. According to a preferred embodiment, for the selection of materials, the material of the balloon 1 and the material of the coating layer generally employ homologous materials so as to ensure a tightness and stable security of hot welding therebetween. The material of the balloon 1 is generally selected from the group consisting of PA, PE, EVA, and alloy material thereof which has a hardness ranged from Shore hardness 55 to 90. The material of the coating layer is generally selected from the group consisting of PA, and PA-Polyether alloy material which has a hardness ranged from Shore hardness 30 to 55.

The coating of the tip coating layer 4 extends to an end surface 32 of the catheter tip 3. The coating layer 4 comprises a round corner setting 41 provided at an outer circumference at a distal end thereof for maximally reducing the injury to the blood vessel during surgery. A catheter wall of the terminal end of the inner catheter 2 has a gradually decreasing thickness toward a tip end thereof and is bonded with an outer extending section of the distal end of the balloon 1 without obvious stepped locations of bonding A catheter wall of the catheter tip 3 formed from an outer extending section of the distal end of the balloon 1 has a gradually decreasing thickness, and an outward extending wall of the coating layer 4 has a gradually increasing thickness. A catheter wall formed by the extending section of the distal end of the balloon 1 and the coating layer 4 has an evenly distributed thickness, and a complex catheter with unhindered and smooth bonds is formed to facilitate the surgery operation.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A balloon dilatation catheter provided with soft coating tip, wherein said balloon dilatation catheter comprises a balloon (1), and an inner catheter (2), characterized in that a distal end of said balloon (1) at a terminal end of said inner catheter (2) extends outward to form a catheter tip (3) with taper inner cavity, wherein a tip coating layer (4) made of a material which is softer than a material of said balloon (1) is coated on said catheter tip (3), wherein a catheter wall of said catheter tip (3) formed from an outer extending section of said distal end of said balloon (1) has a gradually decreasing thickness, wherein an outward extending wall of said coating layer (4) has a gradually increasing thickness, wherein a catheter wall formed by said extending section of said distal end of said balloon (1) and said coating layer (4) has an evenly distributed thickness wherein bond locations are unhindered and smooth.

2. A balloon dilatation catheter provided with soft coating tip, wherein said balloon dilatation catheter comprises a balloon (1), and an inner catheter (2), characterized in that a distal end of said balloon (1) at a terminal end of said inner catheter (2) integrally extends outward to form a catheter tip (3) with taper inner cavity in such a manner that said catheter tip (3) is an integral structure of said balloon, wherein a tip coating layer (4) made of a material which is softer than a material of said balloon (1) is coated on said catheter tip (3), Wherein a catheter wall of said catheter tip (3) formed from an outer extending section of said distal end of said balloon (1) has a gradually decreasing thickness, wherein an outward extending wall of said coating layer (4) has a gradually increasing thickness, wherein a catheter wall formed by said extending section of said distal end of said balloon (1) and said coating layer (4) has an evenly distributed thickness wherein bond locations are unhindered and smooth.

* * * * *